(12) United States Patent
Chen et al.

(10) Patent No.: US 8,846,768 B2
(45) Date of Patent: Sep. 30, 2014

(54) **USE OF COMPOUNDS ISOLATED FROM *EUPHORBIA NERIIFOLIA* FOR TREATING CANCER AND/OR THROMBOCYTOPENIA**

(75) Inventors: Yu-Jen Chen, Taipei (TW); Lie-Chwn Lin, Taipei (TW); Ching-Pin Lin, Taipei (TW)

(73) Assignee: Mackay Memorial Hospital, Taipei (TW)

( * ) Notice: Subject to any disclaimer, the term of this patent is extended or adjusted under 35 U.S.C. 154(b) by 0 days.

(21) Appl. No.: 13/595,170

(22) Filed: Aug. 27, 2012

(65) Prior Publication Data
US 2014/0056995 A1 Feb. 27, 2014

(51) Int. Cl.
*A61K 31/015* (2006.01)
*A61K 33/24* (2006.01)
*A61K 31/336* (2006.01)
*A61K 31/045* (2006.01)

(52) U.S. Cl.
CPC .............. *A61K 31/336* (2013.01); *A61K 33/24* (2013.01); *A61K 31/045* (2013.01)
USPC ........................................................ 514/766

(58) Field of Classification Search
None
See application file for complete search history.

(56) References Cited

U.S. PATENT DOCUMENTS
2012/0276045 A1* 11/2012 Ogbourne et al. ........... 424/85.2

OTHER PUBLICATIONS

Papiya Bigoniya and Avtar Chand Rana, "Radioprotective and In-Vitro Cytotoxic Sapogenin from *Euphorbia neriifolia* (Euphorbiaceae) Leaf", Tropical Journal of Pharmaceutical Research, Dec. 2009; 8 (6): 521-530.*
Kupchan, et al., "Antileukemic Principles Isolated from Euphorbiaceae Plants," Science, 13, Feb. 1976, p. 571-572.*
Abo, K. A., Cytotoxic activity of some semisynthetic derivaties of the diterpene ingol, Fitoterpapia (1987), 58(6), 413-16.*

\* cited by examiner

*Primary Examiner* — San-Ming Hui
*Assistant Examiner* — Jeanmarie Calvillo
(74) *Attorney, Agent, or Firm* — Muncy, Geissler, Olds & Lowe, P.C.

(57) ABSTRACT

Novel Uses of small molecules, particularly, triterpenoids and ingol diterpenes isolated from *Euphorbia neriifolia*, are disclosed herein. The triterpenoids are useful as lead compounds for manufacturing a medicament or a pharmaceutical composition for treating cancer; whereas the ingol diterpenes are useful as lead compounds for manufacturing a medicament or a pharmaceutical composition for treating thrombocytopenia.

6 Claims, 12 Drawing Sheets
(4 of 12 Drawing Sheet(s) Filed in Color)

(A) Control (B) EN28 10μM, 9 days (A) Control (B) EN28 10μM, 5 days (A) Control (B) EN28 10 μM day 3

USE OF COMPOUNDS ISOLATED FROM *EUPHORBIA NERIIFOLIA* FOR TREATING CANCER AND/OR THROMBOCYTOPENIA

BACKGROUND OF THE INVENTION

1. Field of the Invention

The present disclosure relates to novel use of compounds isolated from *Euphorbia neriifolia* for manufacturing a medicament or a pharmaceutical composition for treating cancer and/or thrombocytopenia.

2. Description of Related Art

The leaves and/or latex of plants in *Euphorbia* genus have been used as folk medicines in remote villages and/or tribal areas. For example, latex of *Euphorbia nivulia* is known to enhance wound healing process in mice, and aqueous leaf extract of *Euphorbia nivulia* exhibits toxic and insect growth regulatory effects on cabbage diamondback moth (DBM). In recent years, compounds isolated from plants of *Euphorbia* genus are proved to possess cytotoxicity toward colon cancer cell lines (e.g., MT2 cells) or leukemia cell lines (e.g., CEM cells); and are useful for the development of anti-cancer agents.

In the present study, the medicinal uses of one particular plant in *Euphorbia* genus, i.e., *Euphorbia neriifolia*, were investigated, and the inventors have identified two groups of compounds, i.e., triterpenoids and ingol diterpenes, which are subsequently proved to possess different biological activity. Specifically, the isolated triterpenoids may retard the growth of cancerous cells, whereas the isolated ingol diterpenes induce proliferation and/or differentiation of bone marrow cells.

SUMMARY

The present disclosure is based, at least in part, unexpected discovery that triterpenoids and ingol diterpenes isolated from *Euphorbia neriifolia* may retard the growth of cancerous cells, and/or inducing the proliferation and differentiation of bone marrow cells. The results of this invention suggest that triterpenoids and ingol diterpenes isolated from *Euphorbia neriifolia* are potential lead compounds for use as therapeutic agents for treating cancers; and, Ingol diterpenes isolated from *Euphorbia neriifolia* are potential lead compounds for use as therapeutic agents for treating thrombocytopenia.

Accordingly, the first aspect of this disclosure is directed to a use of a triterpenoid isolated from *Euphorbia neriifolia* for manufacturing an oral medicament for suppressing the growth of cancerous cells or for treating cancer, the oral medicament or pharmaceutical composition comprises a therapeutically effective amount of a compound of formula (I), or a pharmaceutically acceptable salt thereof;

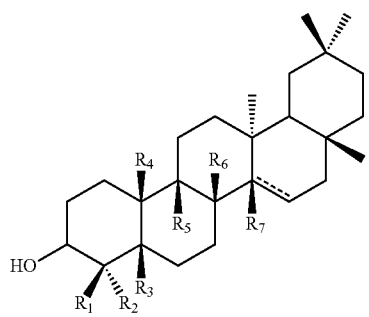

(I)

Wherein ═══ is a single or double bond; $R_1$ is —$CH_3$; $R_2$, $R_3$, $R_4$, $R_5$ and $R_6$ is independently —H or —$CH_3$; and $R_7$ is —$CH_3$ or nil.

The growth of cancerous cells that may be suppressed by the compound of formula (I) are chronic myelogenous leukemia (CML) cells, esophageal cancer cells or pancreatic cancer cells.

In one example, the compound of formula (I) is 3β-friedelinol, in which ═══ is a single bond, $R_1$, $R_3$, $R_5$, and $R_7$ is independently —$CH_3$; and $R_7$, $R_4$ and $R_6$ is independently —H. In another example, the compound of formula (I) is 3β-taraxerol, in which ═══ is a double bond; $R_1$, $R_2$, $R_4$, and $R_6$ is independently —$CH_3$; and $R_3$, and $R_5$ is independently —H; and $R_7$ is nil. In still another example, the compound of formula (I) is 3α-friedelinol, in which ═══ is a single bond; $R_1$, $R_3$, $R_5$, and $R_7$ is independently —$CH_3$; and $R_2$, $R_4$ and $R_6$ is independently —H.

The second aspect of this disclosure is directed to a use of an ingol diterpenes isolated from *Euphorbia neriifolia* for manufacturing a medicament for suppressing the growth of leukemia cells, the medicament or pharmaceutical composition comprises a therapeutically effective amount of a compound of formula (II), or a pharmaceutically acceptable salt thereof;

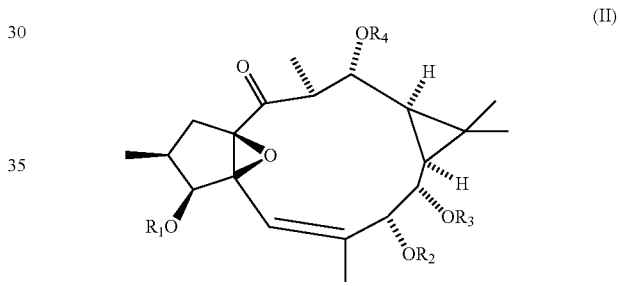

(II)

Wherein $R_1$ and $R_4$ is independently $COCH_3$; $R_2$ is —$COCH_3$,

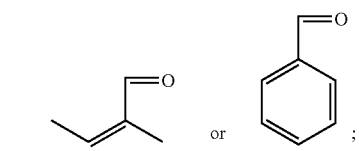

and $R_3$ is $CH_3$,

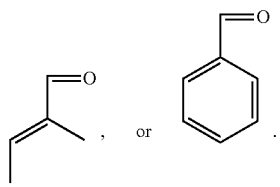

In one example, the compound of formula (II) is 3,7,12-O-triacetyl-8-O-tigloylingol (EN 26), in which $R_1$, $R_2$ and $R_4$ is independently —$COCH_3$, and $R_3$ is

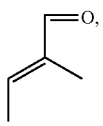

In another example, the compound of formula (II) is 3,7,12-O-triacetyl-8-O-benzoylingol (EN 27), in which $R_1$, $R_2$ and $R_4$ is independently —$COCH_3$; and $R_3$ is

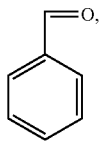

In still another example, the compound of formula (II) is 3,12-O-diacetyl-7-O-angeloyl-8-methoxyingol (EN 28), in which $R_1$ and $R_4$ is independently —$COCH_3$; $R_2$ is

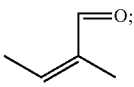

and $R_3$ is —$CH_3$. In yet still another example, to the compound of formula (II) is 3,12-O-diacetyl-8-methoxy-7-O-benzoylingol (EN 29), in which $R_1$ and $R_4$ is independently —$COCH_3$; $R_2$ is

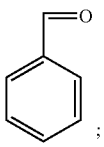

and $R_3$ is —$CH_3$.

The compound of this invention (i.e., the compound of formula (I) or (II)) is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

In some embodiments, the medicament or pharmaceutical composition further comprises another agent that is known to improve the suppression on the growth of cancerous cells. In one preferred example, the medicament or the pharmaceutical composition of this invention further includes a chemotherapeutic agent, such as cisplatin.

It is therefore the third aspect of this disclosure to provide a method of treating cancer in a subject. The method comprises administering to the subject a therapeutically effective amount of the compound of formula (I) or (II) of this disclosure or a pharmaceutically acceptable salt thereof. The cancer treatable by the compound of formula (I) is chronic myelogenous leukemia (CML), esophageal cancer or pancreatic cancer. In one example, the growth of CML is suppressed by 3β-friedelinol. In another example, the growth of CML is suppressed by 3,7,12-O-triacetyl-8-O-tigloylingol (EN 26). In still another example, the growth of CML is suppressed by 3,12-O-diacetyl-7-O-angeloyl-8-methoxyingol (EN 28). In a further example, the growth of esophageal cancer in the subject is suppressed by 3β-friedelinol, without affecting the white blood cell counts, or the function of liver or kidney of the subject. The subject may be a mammal, preferably a human.

In some embodiments, the method further comprises administering to the subject another agent that is known to improve the treatment of cancer before, together with and/or after administering the compound of formula (I) or (II). In some examples, the compound of this invention is administered together with a chemotherapeutic agent. In one preferred example, 3β-friedelinol is administered together with cisplatin to the subject, and is capable of preventing or alleviating the weight loss problem commonly associated with the use of a chemotherapeutic agent.

It is the fourth aspect of this disclosure to provide a use of an ingol diterpene isolated from *Euphorbia neriifolia* for manufacturing a medicament or a pharmaceutical composition for inducing proliferation and/or differentiation of bone marrow cells or treating thrombocytopenia. The medicament or pharmaceutical composition comprises a therapeutically effective amount of a compound of formula (II) or a pharmaceutically acceptable salt thereof,

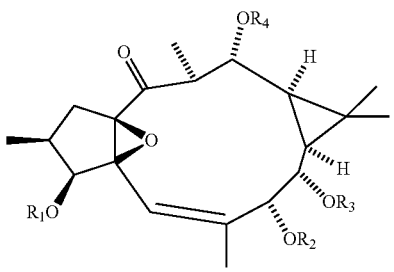

(II)

Wherein $R_1$ and $R_4$ is independently $COCH_3$; $R_2$ is —$COCH_3$,

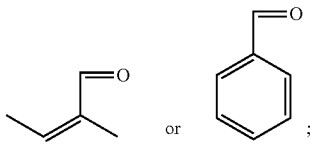

and R₃ is CH₃,

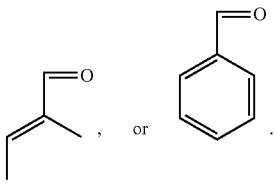

The ingol diterpene or the compound of formula (II) of this invention is present at a level of about 0.1% to 99% by weight, based on the total weight of the pharmaceutical composition. In some embodiments, the compound of formula (II) is present at a level of at least 1% by weight, based on the total weight of the pharmaceutical composition. In certain embodiments, the compound of formula (II) is present at a level of at least 5% by weight, based on the total weight of the pharmaceutical composition. In still other embodiments, the compound of formula (II) is present at a level of at least 10% by weight, based on the total weight of the pharmaceutical composition. In still yet other embodiments, the compound of formula (II) is present at a level of at least 25% by weight, based on the total weight of the pharmaceutical composition.

In one example, the compound of formula (II) is 3,7,12-O-triacetyl-8-O-trigloylingol (EN 26), in which R₁, R₂ and R₄ is independently —COCH₃; and R₃ is

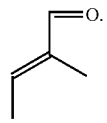

In another example, the compound of formula (II) is 3,7,12-O-triacetyl-8-O-benzoylingol (EN 27), in which R₁, R₂ and R₄ is independently —COCH₃; and R₃ is

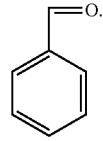

In still another example, the compound of formula (II) is 3,12-O-diacetyl-7-O-angeloyl-8-methoxyingol (EN 28), in which R₁ and R₄ is independently —COCH₃; R₂ is

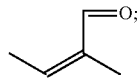

and R₃ is —CH₃. In yet still another example, the compound of formula (II) is 3,12-O-diacetyl-8-methoxy-7-O-benzoylingol (EN 29), in which R₁ and R₄ is independently —COCH₃; R₁ is

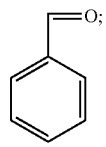

and R₃ is —CH₃.

It is therefore the fifth aspect of this disclosure to provide a method of treating thrombocytopenia in a subject. The method comprises administering to the subject an effective amount of the compound of formula (II) of this disclosure or a pharmaceutically acceptable salt thereof so as to induce differentiation of leukemia cells or bone marrow cells to megakaryocytic cells. The leukemia cells are chronic myelogenous leukemia cells or erythroleukemia cells; and the bone marrow cells are normal bone marrow cells. The subject may be a mammal, preferably a human. In one preferred example, the compound of formula (II) is 3,12-O-diacetyl-7-O-angeloyl-8-methoxyingol (EN 28), in which R₁ and R₄ is independently —COCH₃; R₂ is

and R₃ is —CH₃.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, wherein.

DETAILED DESCRIPTION

Figure 1:
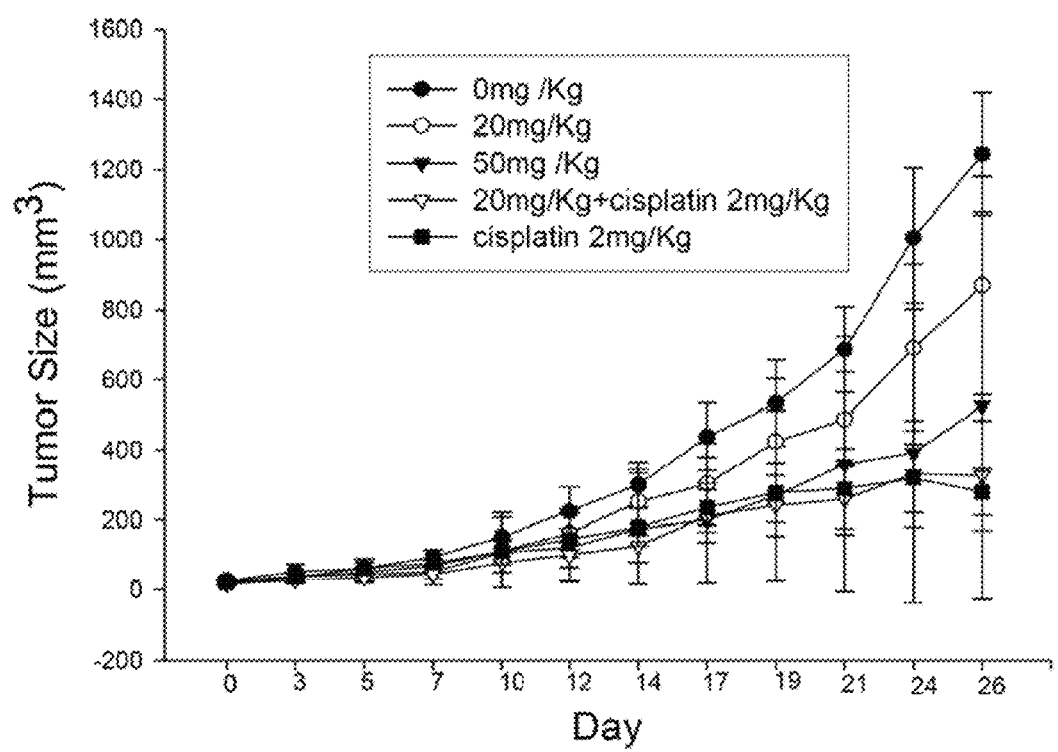
FIG. 1 illustrates the effects of EN 22 on the tumor size of cisplatin-treated animals in accordance with one embodiment of this invention.

The detailed description provided below in connection with the appended drawings is intended as a description of the present invention and is not intended to represent the only forms in which the present invention may be constructed or utilized.

In the context of this disclosure, a number of terms shall be used.

The term "treating" or "treatment" as used herein refers to administering a compound of this invention to arrest the growth of at least 45%, 50%, 55%, 60% or 65% of the cancerous cells, preventing them from multiplying, and hence results in the reduction of the size of the cancer. Therefore, the term "treating" or "treatment" as used herein also refers to kill or induce apoptosis of the cancerous cells.

The term "an effective amount" as used herein refers to an amount effective, at dosages, and for periods of time necessary, to achieve the desired therapeutically desired result with respect to the treatment of cancer or thrombocytopenia.

The terms "compounds", "compositions", "agent" or "medicament" are used interchangeably herein to refer to a compound or compounds or composition of which, when administered to a subject (human or animal) induces a desired pharmacological and/or physiological effect by local and/or systemic action.

The term "administered", "administering" or "administration" are used interchangeably herein to refer means either directly administering a compound or a composition of the present invention, or administering a prodrug, derivative or analog which will form an equivalent amount of the active compound within the body.

The term "subject" or "patient" refers to an animal including the human species that is treatable with the compositions and/or methods of the present invention. The term "subject" or "patient" intended to refer to both the male and female gender unless one gender is specifically indicated. Accordingly, the term "subject" or "patient" comprises any mammal, preferably a human, which may benefit from treatment by the compound of this disclosure.

The present disclosure is based, at least in part, unexpected discovery that triterpenoids and ingol diterpenes isolated from *Euphorbia neriifolia* may retard the growth of cancerous cells, and/or inducing the proliferation and/or differentiation of bone marrow cells. Therefore, these active compounds are potential lead compounds for use as therapeutic agents for treating cancer or thrombocytopenia.

The active compound isolated from *Euphorbia neriifolia* has a formula (I) or (II). In some examples, the compound has a formula (I),

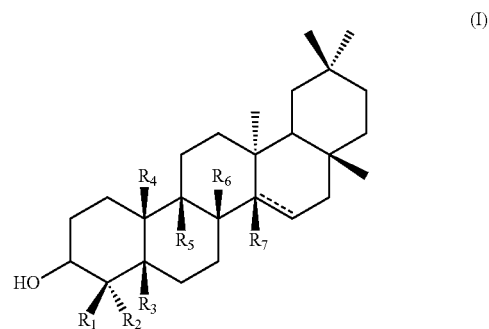

(I)

Wherein ----- is a single or double bond; $R_1$ is —$CH_3$; $R_2$, $R_3$, $R_4$, $R_5$ and $R_6$ is independently —H or —$CH_3$; and $R_7$ is —$CH_3$ or nil.

Specifically, the compound of formula (I) may be selected from the group consisting of,

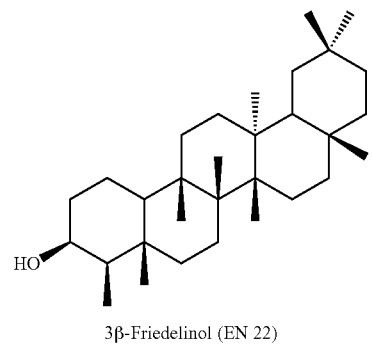

3β-Friedelinol (EN 22)

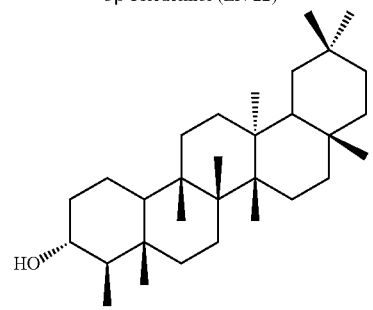

3α-Friedelinol (EN 25)

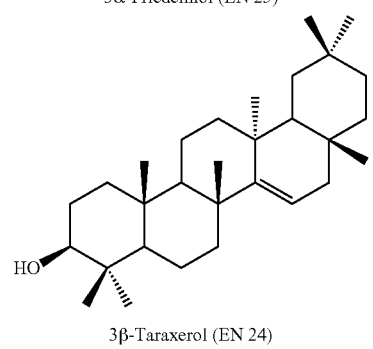

3β-Taraxerol (EN 24)

-continued
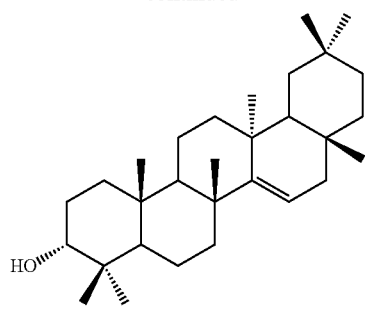
3α-Taraxerol (EN 23)
In other examples, the compound has a formula (II),
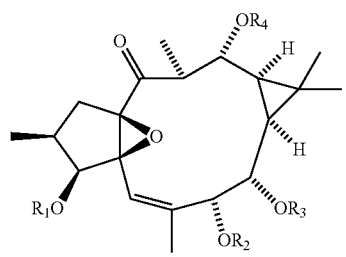
(II)
Wherein R₁ and R₄ is independently —COCH₃; R₂ is —COCH₃,
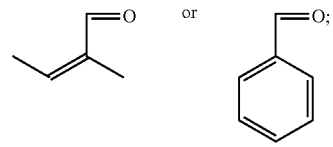 or
and R₃ is —CH₃,
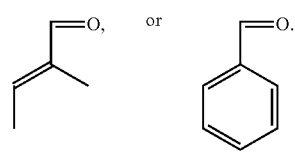 or
Specifically, the compound of formula (II) may be any of the followings,
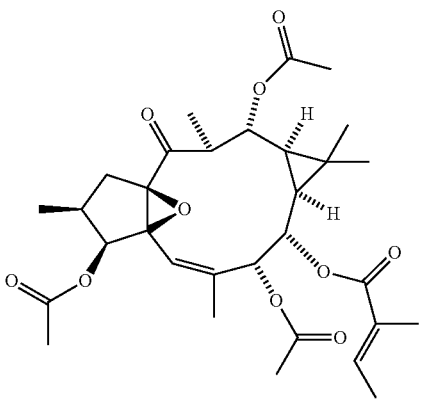
3,7,12-O-triacetyl-8-O-tiglcylingol (EN 26)
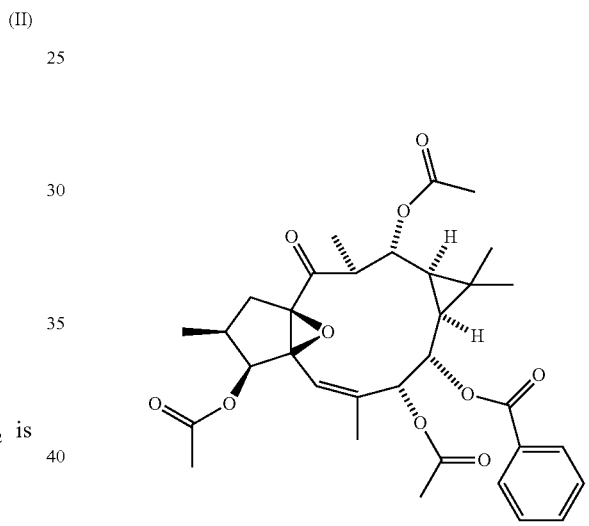
3,7,12-O-triacetyl-8-O-benzoylingol (EN 27)
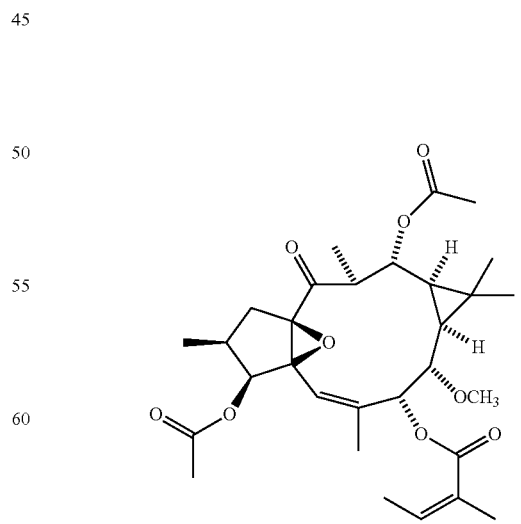
3,12-O-diacetyl-7-O-angeloyl-8-methoxyingol (EN 28)

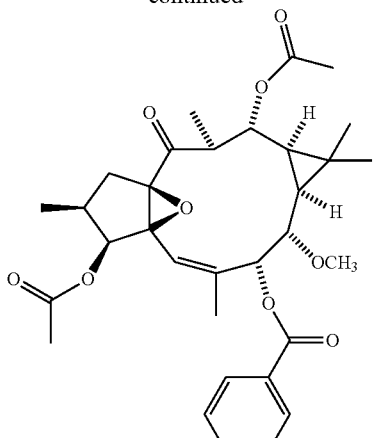

3,12-O-diacetyl-8-methoxy-7-O-benzoylingol (EN 29)

The compound of formula (I) or (II) may be isolated form *Euphorbia neriifolia*. The aerial part of the plant, *Euphorbia neriifolia*, is collected and extracted with a suitable organic solvent in accordance with any method that is well known in the art. The organic solvent may include, but is not limited to, alcohols (e.g., methanol, ethanol, propanol and isopropanol), esters (e.g., acetic acetate), alkanes (e.g., hexanes and cyclohexanes), and alkylhalides (e.g., mono- or di-chloromethane, mono- or di-chloroethane). In one preferred example, the organic solvent is an alcohol, such as ethanol. According to embodiments of the present disclosure, the dried organic extract is then suspended in water and further extracted with ethyl acetate; the ethyl acetate extract is subsequently subject to silica gel chromatography until a pure compound is identified. According to embodiments of the present disclosure, the silica gel column is eluted with a series of solvent mixtures; and each fraction is collected and subject to further silica gel chromatography and/or preparative HPLC until a pure compound is obtained. In one preferred embodiment, the silica gel is eluded with a gradient of a solvent mixture that consists of ethyl acetate and n-hexane (0-100%); and a total of 23 fractions are collected. In one example, the silica gel is eluded in sequence, with hexane, and a mixture of 95% hexane and 5% ethyl acetate. In another example, the silica gel is eluded in sequence, with hexane, and a mixture of 80% hexane and 20% ethyl acetate. In still another example, the silica gel is eluded in sequence, with 5% ethyl acetate and benzene. Optionally, solvent re-crystallization may also be used to help isolating the pure compound.

Accordingly, the first aspect of this disclosure is directed to a use of the compound of this invention (i.e., compounds of formula (I) or (II)) for manufacturing a medicament for suppressing the growth of cancerous cells, or for treating cancer, the medicament or pharmaceutical composition comprises a therapeutically effective amount of the compound of this invention described above or a pharmaceutically acceptable salt thereof.

In one example, the compound of formula (I) is 3β-friedelinol (EN 22), in which ═══ is a single bond; $R_1$, $R_3$, $R_5$, and $R_7$ is independently —$CH_3$; and $R_2$, $R_4$ and $R_6$ is independently —H. In another example, the compound of formula (I) is 3β-taraxerol (EN 24), in which ═══ is a double bond; $R_1$, $R_2$, $R_4$, and $R_6$ is independently —$CH_3$; and $R_3$, and $R_5$ is independently —H; and $R_7$ is nil. In still another example, the compound of formula (I) is 3α-friedelinol (EN 25), in which ═══ is a single bond; $R_1$, $R_3$, $R_5$, and $R_7$ is independently —$CH_3$; and $R_2$, $R_4$ and $R_6$ is independently —H. In still yet another example, the compound of formula (I) is 3α-taraxerol, in which ═══ is a double bond; $R_1$, $R_2$, $R_4$, and $R_6$ is independently —$CH_3$; and $R_3$ and $R_5$ is independently —H; and $R_7$ is nil.

In another example, the compound of formula (II) is 3,7,12-O-triacetyl-8-O-trigloylingol (EN 26), in which $R_1$, $R_2$ and $R_4$ is independently —$COCH_3$; and $R_3$ is

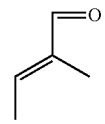

In another example, the compound of formula (II) is 3,7,12-O-triacetyl-8-O-benzoylingol (EN 27), in which $R_1$, $R_2$ and $R_4$ is independently —$COCH_3$; and $R_3$ is

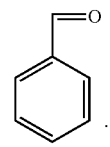

In still another example, the compound of formula (II) is 3,12-O-diacetyl-7-O-angeloyl-8-methoxyingol (EN 28), in which $R_1$ and $R_4$ is independently —$COCH_3$; $R_2$ is

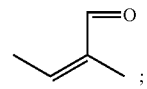

and $R_3$ is —$CH_3$. In yet still another example, the compound of formula (II) is, in which $R_1$ and $R_4$ is independently —$COCH_3$; $R_2$ is

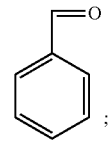

and $R_3$ is —$CH_3$.

The growth of cancerous cells, such as chronic myelogenous leukemia (CML) cells, human erythroleukemia (HEL) cells, esophageal cancer cells or pancreatic cancer cells, may be inhibited or suppressed by the compound of formula (I) or (II) at a concentration from about 1 to 10 μM, such as 1, 2, 3, 4, 5, 6, 7, 8, 9 or 10 μM. In one example, the ex vivo growth of esophageal cancerous cells is inhibited for about 50% and 60% at about 1 and 10 μM of 3β-friedelinol (EN22), respectively. In still another example, the ex vivo growth of esophageal cancerous cells is inhibited by 3α-taraxerol (EN25) for about 50% at a concentration of about 1 μM, and about 60% at a concentration of about 10 μM. In a further example, the ex vivo growth of CML cells is suppressed for about 45% by about 10 μM 3β-friedelinol (EN22). In still another example, the ex vivo growth of CML cells is suppressed for about 40% by about 10 μM 3,7,12-O-triacetyl-8-O-trigloylingol (EN 26). In other example, the ex vivo growth of CML cells is suppressed for about 50% by about 10 μM 3,12-O-diacetyl-7-O-angeloyl-8-methoxyingol (EN 28). In a further example, the in vitro growth of human erythroleukemia (HEL) cells is inhibited for about 40% by 3,12-O-diacetyl-7-O-angeloyl-8-methoxyingol (EN 28) at a dose of about 2.5 μM, about 55% at 5 μM, and about 60% at 10 μM.

Accordingly, this disclosure provides a method of treating cancer in a subject. The method includes steps of administering to the subject an effective amount of any of the compound of formula (I) or (II) described above or a pharmaceutically acceptable salt thereof.

In some embodiments, the effective amount of the compounds of formula (I) or (II) administered to the subject is from about 1 to 100 mg/Kg body weight of the subject by oral ingestion, intravenous or intramuscular injection. Preferably, the compounds of formula (I) or (II) are administered orally. The amount is administered to the subject at about 10, 20, 30, 40, 50, 60, 70, 80, 90 or 100 mg/Kg body weight of the subject per day, preferably about 30 to 70 mg/Kg body weight of the subject, such as 30, 40, 50, 60 or 70 mg/Kg body weight of the subject per day; and more preferably about 50 mg/Kg body weight of the subject per day. The dose can be administered in a single dosage, or alternatively in more than one dosage.

In some embodiments, the method further includes the step of administering another agent that is known to improve the treatment of cancer, before, together with and/or after administering the compound of formula (I) or (II) of this invention. In one specific example, 2 mg/Kg of cisplatin is intraperitoneally administered together with orally administered 50 mg/Kg of 3β-friedelinol (EN22) to a subject suffering from esophageal cancer for a period of at least 25 days; and such combinational treatment is capable of preventing or reducing the body weight loss of the subject commonly caused by a chemotherapeutic agent. In another example, oral administration of 50 mg/Kg of 3β-friedelinol (EN22) together with 2 mg/Kg of cisplatin to a subject suffering from esophageal cancer for a period of at least 24 days, and the combinational treatment exhibits small or negligible effects on the white blood cell counts, and/or liver or kidney function of the subject.

Accordingly, this disclosure provides a medicament or pharmaceutical composition for inhibiting the growth of cancerous cells or for treating cancers. The medicament or pharmaceutical composition comprises an effective amount of the compound of formula (I) or (II), and a pharmaceutically acceptable excipient thereof. Generally, the compound of formula (I) or (II) is present at a level of about 0.1% to 99% by weight, based on the total weight of the pharmaceutical composition. In some embodiments, the compound of formula (I) or (II) is present at a level of at least 1% by weight, based on the total weight of the pharmaceutical composition. In certain embodiments, the compound of formula (I) or (II) is present at a level of at least 5% by weight, based on the total weight of the pharmaceutical composition. In still other embodiments, the compound of formula (I) or (II) is present at a level of at least 10% by weight, based on the total weight of the pharmaceutical composition. In still yet other embodiments, the compound of formula (I) or (II) is present at a level of at least 25% by weight, based on the total weight of the pharmaceutical composition.

Accordingly, the second aspect of this disclosure is directed to a use of the compound of formula (II) for manufacturing a medicament for inducing proliferation and/or differentiation of bone marrow cells or for treating thrombocytopenia. The medicament or pharmaceutical composition comprises a therapeutically effective amount of a compound of formula (II) or a pharmaceutically acceptable salt thereof,

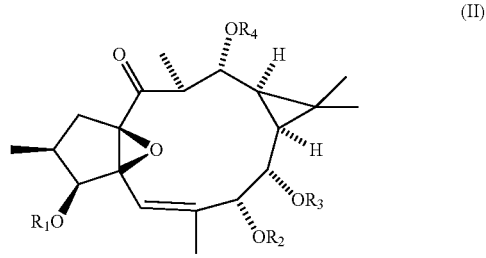

(II)

Wherein $R_1$ and $R_4$ is independently $COCH_3$; $R_2$ is —$COCH_3$,

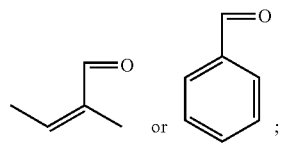

and $R_3$ is $CH_3$,

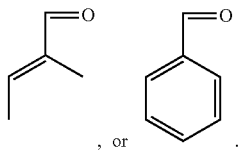

The ingol diterpene or the compound of formula (II) of this invention is present at a level of about 0.1% to 99% by weight, based on the total weight of the pharmaceutical composition. In some embodiments, the compound of formula (II) is present at a level of at least 1% by weight, based on the total weight of the pharmaceutical composition. In certain embodiments, the compound of formula (II) is present at a level of at least 5% by weight, based on the total weight of the pharmaceutical composition. In still other embodiments, the compound of formula (II) is present at a level of at least 10% by weight, based on the total weight of the pharmaceutical composition. In still yet other embodiments, the compound of formula (II) is present at a level of at least 25% by weight, based on the total weight of the pharmaceutical composition.

In one example, the compound of formula (II) is 3,7,12-O-triacetyl-8-O-trigloylingol (EN 26), in which $R_1$, $R_2$ and $R_4$ is independently —$COCH_3$; and $R_3$ is

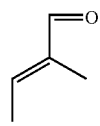

In another example, the compound of formula (II) is 3,7,12-O-triacetyl-8-O-benzoylingol (EN 27), in which $R_1$, $R_2$ and $R_4$ is independently —$COCH_3$; and $R_3$ is

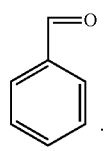

In still another example, the compound of formula (II) is 3,12-O-diacetyl-7-O-angeloyl-8-methoxyingol (EN 28), in which $R_1$ and $R_4$ is independently —$COCH_3$; $R_2$ is

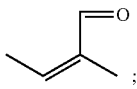

and $R_3$ is $CH_3$. In yet still another example, the compound of formula (II) is 3,12-O-diacetyl-8-methoxy-7-O-benzoylingol (EN 29), in which $R_1$ and $R_4$ is independently —$COCH_3$; $R_2$ is

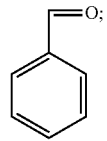

and $R_3$ is —$CH_3$.

According to some embodiments, leukemia cells (e.g., CML cells or HEL cells) or normal bone marrow cells may be induced to differentiate into megakaryocytes by the treatment of the compound of formula (II). Megakaryocytes are bone marrow cells responsible for the production of platelets, which are necessary for normal blood clotting. Accordingly, the compounds of formula (II) are potential lead compounds for treating thrombocytopenia. In one example, 3,12-O-diacetyl-7-O-angeloyl-8-methoxyingol (EN 28) induces the differentiation of HEL cells into megakaryocytes at a concentration of 10 µM. In another example, normal bone marrow cells are differentiated into megakaryocytes by about 1.25 µM to about 5 µM of 3,12-O-diacetyl-7-O-angeloyl-8-methoxyingol (EN 28).

Accordingly, this disclosure provides a method of treating thrombocytopenia in a subject. The method includes steps of administering to the subject an effective amount of any of the compound of formula (II) described above or a pharmaceutically acceptable salt thereof.

In some embodiments, the effective amount of the compounds of formula (II) administered to the subject is from about 1 to 100 mg/Kg body weight of the subject by oral ingestion, intravenous or intramuscular injection. Preferably, the compounds of formula (II) are administered orally. The amount is administered to the subject at about 10, 20, 30, 40, 50, 60, 70, 80, 90 or 100 mg/Kg body weight of the subject per day, preferably about 30 to 70 mg/Kg body weight of the subject, such as 30, 40, 50, 60 or 70 mg/Kg body weight of the subject per day; and more preferably about 50 mg/Kg body weight of the subject per day. The dose can be administered in a single dosage, or alternatively in more than one dosage.

In general, the compounds of this invention (e.g., compound of formula (1) or (II)) may be administered by any suitable route, for example, orally in capsules, sachets, suspensions or tablets; or by parenterally administration. Parenterally administration can include, for example, systemic administration such as oral, intramuscular, intravenous, subcutaneous, or intraperitoneal injection. The compound can also be administered transdermally either topically or by inhalation (e.g., intrabronichial, intranasal, oral inhalation or intranasal drops), or rectally, alone or in combination with conventional pharmaceutically acceptable excipients. In preferred embodiments, the compounds of this invention are administered orally (e.g., dietary) to the subject.

For oral administration, the compounds of the present invention may be formulated into solid dosage forms include, but are not limited to, tablets, capsules, and sachets. Each tablet may contain various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Materials in this connection also include lactose or milk sugar as well as high molecular weight polyethylene glycols. The described solid dosage forms may optionally contain coatings and shells, such as enteric coatings, and coatings for modifying the release rate of any of the ingredients. Examples of such coatings are well known in the art. In one example, the pharmaceutical compositions of this disclosure are formulated into tablets. In another example, the pharmaceutical compositions of this disclosure are powders that are encapsulated in soft and hard gelatin capsules or packed in biodegradable pharmaceutical sachets. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

In some embodiments, the pharmaceutical compositions of this disclosure are liquid dosage forms for oral administration. The liquid formulation may further include a buffering agent to maintain a desired pH. The liquid dosage formulations may also be filled into soft gelatin capsules. For example, the liquid may include a solution, suspension, emulsion, microemulsion, precipitate or any desired liquid media carrying the compound of formula (I) or (II), a pharmaceutically acceptable derivative, stereoisomer, metabolite, salt or solvate thereof, or a combination thereof. The liquid may be designed to improve the solubility of the compound of formula (I) or (II), or a pharmaceutically acceptable salt thereof to form a drug-containing emulsion or disperse phase upon release. In such forms, the active ingredient is mixed with at least one pharmaceutically acceptable excipient including, but is not limited to, as described above.

For parenteral administration, the compounds of the present invention may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For transmucosal administration, the medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

It will be appreciated that the dosage of compounds of the present invention will vary from patient to patient not only for the particular compound or composition selected, the route of administration, and the ability of the compound (alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the respective testing measurements.

The present invention will now be described more specifically with reference to the following embodiments, which are provided for the purpose of demonstration rather than limitation.

EXAMPLES

Materials and Methods

Cell Lines and Animals

Cell lines used in the present disclosure include human chronic is myelogenous leukemia (CML) cell line K562, erythroleukemia HEL cells, human pancreatic carcinoma epithelial-like cell line PANC-1, human esophageal squamous cell carcinoma line 81T/VGH, human esophageal adenocarcinoma line BE-3 and human esophageal adenocarcinoma cell line SKGT4. Each cell lines were cultured and maintained in Dulbecco's modified Eagle media (DMEM) supplemented with 10% fetal calf serum, 100 IU/ml penicillin, 100 µg/ml streptomycin, and 2 mM glutamine in 5% $CO_2$ at 37° C.

Athymic BALB/c-nu nude mice (4 weeks old) were obtained from the National Laboratory Animal Center (Taipei, Taiwan) and were kept in a pathogen-free facility with ad libitum access to water and laboratory chow. A solution of 81T/VGH cells was injected into the subcutaneous tissue to establish a xenograft tumor. All animal experiments were performed in accordance with the guidelines of the Animal Welfare Committee of Mackay Memorial Hospital (Taiwan, R.O.C.).

MTT Assay

MTT assay is a colorimetric assay that measures the activity of enzymes (i.e., reductase) that reduce (3-(4,5-dimethylthiazol-2-yl)-2,5-diphenyltetrazoliumbromide (MTT), a yellow tetrazole, to purple formazan, in living cells. This reduction only takes place when cells are alive; hence MTT assay is generally used to assess the viability and proliferation of cells. Briefly, cells were challenged with various doses of the tested compound (e.g., the compound of formula (I) or (II)) for 24, 48 or 72 hours. Then, MTT dye (500 µg/ml) was added and the reaction was allowed to proceed for 4 hours before being terminated by the addition of 500 µl of isopropanol. The absorbance of the solution at 570 nm was measured by spectrophotometer.

Cell Cycle Analysis

Cultured cells with or without pre-treatment of the compounds of this invention (i.e., the compound of formula (I) or (II)) were harvested from the cultured media and fixed by incuating with 75% iced cold ethanol at 4° C. for at least over night. The fixed cells were then warmed up to room temperature and treated with RNAase A for about 30 min. Precipitated cells were collected by centrifugation and re-suspended in a buffer solution containing propidium iodine (20 µg/ml) before being subject to flow cytometry analysis, where cell numbers at respective cell cycles were determined.

Immunoblot Analysis

Cultured cells were lysed by use of well known lysing buffer, and total amount of proteins were determined by Bradford method. The extracted raw proteins (about 50-100 µg) were loaded to 0.15% sodium dodecyl sulfate polyacrylamide gel, and proteins therein were separated by electrophoresis. The separated proteins were then transferred to nitrocellulose membrane and non-specific binding was removed by TBST buffer (0.8% NaCl, 0.02% KCl, 25 mM Tris-HCl/pH 8.0 and 0.1% Tween-20) containing 4% skim milk. Antibodies including p-Jak2, Jak2, p-stat3-2, stat3, p-stat5, stat5, and GAPDH (purchased from Transduction Laboratories, Lexington, Ky., USA), were respectively dissolved in TBST buffer containing 2% skim milk and incubated with the separated protein bands at 4° C. for at least over night; followed by incubation with horseradish conjugated secondary antibodies at room temperature for about 30 min, and then detected by ECL chemiluminesance detection kit (Amersham Pharmacia Biotech, US).

Liu's Staining

Cells were transferred to a glass coverslide and covered with solution A (0.5 g of methylene blue and 1.7 g of Eosin yellow dissolved in 1,000 ml of ethanol). After 45 seconds, solution B (1.3 g of azure, 1.4 g of methylene blue, 23.38 g of $Na_2HPO_4$, 6.5 g of $KH_2PO_4$, dissolved in 1,000 ml of distilled water) was added in the proportion of 2 parts of B to 1 part of A. Mixed the solutions well by blowing the surface. The slide was left standing for 90 seconds and then washed off the staining solution rapidly by running water. The morphology of stained cells was then examined by observation under microscope.

Generation of Esophageal Squamous Carcinomas and In Vivo Therapy

For inoculated tumor model, $1\times10^5$ 81T/VGH cells were injected subcutaneously to lab animals to generate s.c. tumors ($5\times10^5$ cells per injection) on day 1. The needle hole was sealed with an electric coagulator (Aaron, Petersburg, Fla., USA) immediately after the withdrawal of the needle to avoid leakage of the injected substance. The incision was subsequently sutured.

Tumor sizes were measured using calipers, and tumor volume was calculated using the formula: volume=width$^2$×length×0.52. The average body weight (BW) of the animals was measured daily, and the concentration of the test compound(s) (i.e., EN22, cisplatin, or a combination thereof) in their drinking water was adjusted proportionally to the BW respectively at the indicated dosage and time.

After treatment, mice were sacrificed and their white blood cells (WBC) counts were measured. Tumor burdens were determined by the total volume of all the tumor nodules with diameter greater than 3 mm.

STAT3 RNAi Assay

The murine stat3 target sequence from positions 134 to 158 (5'-TGG CCC AAT GGA ATC AGC TAC AGC A-3' (SEQ ID NO: 1)) was selected for the preparation of stat3 siRNA (5'-UGG CCC AAU GGA AUC AGC UAC AGC A-3' (SEQ ID NO: 2)). Scrambled RNAs were employed as a negative control and were synthesized by PCR-derived siRNA expression cassettes according to the manufacturer's instructions and were then cloned into pSEC™ hygro plasmid (Ambion).

Mouse HEL cells were transfected with the plasmids (i.e., plasmids containing the nucleic acid for the stat3 siRNA or scramble RNAs) described above with the aid of the lipofectamine 2000 (Invitrogen, Carlsbad, Calif. USA). Specifically, 5 µg pSEC™ hygro plasmid contained murine stat3 siNAs and 9 µl lipofectamine 2000 were allowed to form complexes in a period of 25 min at room temperature in antibiotic-free DMEM medium. The complexes were then added to HEL cells maintained and cultured in 6-well dishes and further incubated for another 24 hrs. For the selection of cells with high expression rate of siRNA, stable clones of murine stat3 siRNA expressed cells and negative control siRNA (i.e., scrambled RNA) were selected by use of 500 µg/ml hygromycin contained medium, and the selected clones were maintained in 250 µg/ml hygromycin contained medium. The transfection of murine stat3 siRNAs in HEL cells was confirmed by the detection of murine stat3 gene expression in protein level by immunoblot assay.

Example 1

Purification and Identification of Compounds of Formula (I) or (II) from *Euphorbia neriifolia*

The aerial parts of fresh *Euphorbia neriifolia* Linn. (18.2 kg) were sliced and extracted with ethanol (40 L×3) under reflux. The dried ethanolic extract (368 g) was suspended in water (1 L), then extracted successively with EtOAc, and n-BuOH (each 1 L×3) to give EtOAc (82 g), n-BuOH (37 g), and water (304 g) fractions, respectively. The EtOAc fraction (80 g) was subjected to column chromatography on silica gel (10×120 cm), with a gradient of EtOAc in n-hexane (0-100%) and total of 23 fractions (Frs. 1-23) were collected based on TLC tracing.

Fractions 5 and 6 (3.5 g) were pooled together and subsequently chromatographed on a silica gel eluted by 5% EtOAc in n-hexane, to give rise to EN 22 and EN 23. Fraction 8 (10.4 g) was chromatographed on a silica gel eluted with 5% EtOAc/n-hexane that give rise to eight sub-fractions (i.e., Frs. 8-1 to 8-8). Solid precipitates were collected from Frs. 8-4 and Fr.8-6 and re-crystallized with EtOAc/n-hexane that gave rise to EN 24 and EN 25, respectively. The filtrate from Frs.8-4 and 8-6 were combined, and EN 24 and EN 25 were identified by silica gel column chromatography (5% EtOAc in n-hexane).

Fraction 14 (3.9 g) was chromatographed on a silica gel by eluting the gel with 20% EtOAc/n-hexane, which gave 10 sub-fractions, i.e., Frs. 14-1 to 14-10. Fraction 14-5 (1.1 g) was purified by a silica gel (5% EtOAc/benzene) and a preparative HPLC (column: Cosmosil 5C18-AR-II, 20×250 mm, 5 µm, solvent: 65% ACN/H$_2$O, flow rate: 18 ml/min) to give EN 28 and EN 29. Fraction 14-6 (0.6 g) was purified by a silica gel (2×30 cm, 12-26 µm, Knauer) that was eluted with 5% EtOAc/benzene to get EN 26, and EN 27.

The isolated compounds (i.e., EN22 to EN29) were subject to spectral analysis including MS, $^1$H-NMR and $^{13}$C-NMR, the respective spectra data are listed below, as well as in Tables 1 and 2.

3β-Friedelinol (EN 22): White powder; $^1$H NMR (pyridine-d$_5$) δ 0.91 (3H, s, H-25), 0.97 (3H, s, H-26), 0.98 (3H, s, H-29), 1.02 (3H, s, H-27), 1.05 (3H, s, H-30), 1.16 (3H, d, J=7.2 Hz, H-23), 1.17 (3H, s, H-28), 1.27 (3H, s, H-24), 1.00 (1H, m, H-6a), 1.65 (1H, m, H-2a), 1.80 (1H, dt, J=13.2, 3.0 Hz, H-6b), 2.14 (1H, dd, J=13.2, 3.0 Hz, H-2b), 3.96 (1H, s, H-3); $^{13}$C NMR (pyridine-d$_5$, CDCl$_3$) see Table 1; EIMS m/z 428 [M]$^+$.

3α-Taraxerol (EN 23): White powder; $^1$H NMR (pyridine-d$_5$) δ 0.88 (6H, s, H-27, −28), 0.91 (3H, s, H-24), 0.96 (3H, s, H-30), 0.97 (3H, s, H-25), 0.98 (3H, s, H-29), 1.13 (3H, s, H-26), 1.19 (3H, s, H-23), 3.61 (1H, s, H-3), 5.57 (1H, dd, H=7.8, 3.0 Hz, H-15); $^{13}$C NMR (pyridine-d$_5$, CDCl$_3$) see Table 1; EIMS m/z 426 [M]$^+$.

3β-Taraxerol (EN 24): White powder; $^1$H NMR (pyridine-d$_5$) δ 0.80 (1H, d, J=10.0 Hz, H-5), 0.89 (3H, s, H-28), 0.95 (3H, s, H-25), 0.97 (3H, s, H-30), 0.98 (3H, s, H-27), 0.99 (3H, s, H-29), 1.06 (3H, s, H-24), 1.11 (3H, s, H-26), 1.23 (3H, s, H-23), 3.43 (1H, dd, J=10.5, 5.0 Hz, H-3), 5.61 (1H, dd, H=8.0, 3.5 Hz, H-15); $^{13}$C NMR (pyridine-d$_5$, CDCl$_3$) see Table 1; EIMS m/z 426 [M]$^+$.

3α-Friedelinol (EN 25): White powder; $^1$H NMR (pyridine-d$_5$) δ 0.81 (3H, s, H-25), 0.95 (3H, s, H-26), 0.97 (6H, s, H-27, −29), 1.03 (3H, s, H-30), 1.18 (3H, d, J=6.6 Hz, H-23), 1.16 (3H, s, H-28), 0.81 (3H, s, H-24), 1.04 (1H, m, H-6a), 1.59 (1H, m, H-2a), 1.77 (1H, td, J=13.2, 3.0 Hz, H-6b), 2.32 (1H, m, H-2b), 3.58 (1H, m, H-3); $^{13}$C NMR (pyridine-d$_5$, CDCl$_3$) see Table 1; EIMS m/z 428 [M]$^+$.

3,7,12-O-Triacetyl-8-O-tigioylingol (EN 26) White powder; $^1$H and $^{13}$C NMR (CD$_3$OD) see Table 2; ESIMS m/z 597 [M+Na]$^+$.

3,7,12-O-Triacetyl-8-O-benzoylingol (EN 27): White powder; $^1$H and $^{13}$C NMR (CD$_3$OD) see Table 2; ESIMS m/z 619 [M+Na]$^+$.

3,12-O-Diacetyl-7-O-angeloyl-8-methoxyingol (EN 28): White powder; $^1$H and $^{13}$C NMR (CD$_3$OD) see Table 2; ESIMS m/z 569 [M+Na]$^+$.

3,12-O-Diacetyl-8-methoxy-7-O-benzoylingol (EN 29): White powder; $^1$H and $^{13}$C NMR (CD$_3$OD) see Table 2; ESIMS m/z 591 [M+Na]$^+$.

TABLE 1

¹³C NMR Data of Triterpenoids (EN 22 to EN 25)

|  | EN 22 3β-friedelinol | | EN 25 3α-friedelinol | | EN 24 3β-taraxerol | | EN 23 3α-taraxerol | |
| --- | --- | --- | --- | --- | --- | --- | --- | --- |
| No. | ¹³C (py-d₅) | ¹³C (CDCl₃) | ¹³C (py-d₅) | ¹³C (CDCl₃) | ¹³C (py-d₅) | ¹³C (CDCl₃) | ¹³C (py-d₅) | ¹³C (CDCl₃) |
| 1 | 16.6 | 15.8 | 20.1 | 19.6 | 38.2 | 37.7 | 32.9 | 32.2 |
| 2 | 36.6 | 36.1 | 37.8 | 36.7 | 28.1 | 27.1 | 26.2 | 25.1 |
| 3 | 71.4 | 72.7 | 70.9 | 72.2 | 78.1 | 79.1 | 75.2 | 76.2 |
| 4 | 50.0 | 49.2 | 54.0 | 53.2 | 39.3 | 39.0 | 37.7 | 37.4 |
| 5 | 38.5 | 37.8 | 38.3 | 38.1 | 55.0 | 55.5 | 49.5 | 49.3 |
| 6 | 42.3 | 41.7 | 41.8 | 41.4 | 19.2 | 18.8 | 19.0 | 18.7 |
| 7 | 18.0 | 17.5 | 18.2 | 17.8 | 41.7 | 41.3 | 41.7 | 41.2 |
| 8 | 53.5 | 53.2 | 53.2 | 53.0 | 39.4 | 38.8 | 39.4 | 39.1 |
| 9 | 37.4 | 37.1 | 37.2 | 37.0 | 49.5 | 49.3 | 49.3 | 48.9 |
| 10 | 61.9 | 61.3 | 60.6 | 60.1 | 38.3 | 38.0 | 38.4 | 38.0 |
| 11 | 36.0 | 35.3 | 35.8 | 35.5 | 17.8 | 17.5 | 17.8 | 17.4 |
| 12 | 30.9 | 30.6 | 30.8 | 30.6 | 34.0 | 33.7 | 34.0 | 33.7 |
| 13 | 38.6 | 38.4 | 38.4 | 38.3 | 37.8 | 37.6 | 37.7 | 37.5 |
| 14 | 39.9 | 39.7 | 39.8 | 39.7 | 158.4 | 158.1 | 158.5 | 158.2 |
| 15 | 32.5 | 32.3 | 32.5 | 32.4 | 117.1 | 116.9 | 116.9 | 116.7 |
| 16 | 36.4 | 35.5 | 36.3 | 36.1 | 37.9 | 37.7 | 37.9 | 37.7 |
| 17 | 30.2 | 30.0 | 30.1 | 30.0 | 36.0 | 35.8 | 36.0 | 35.8 |
| 18 | 43.1 | 42.8 | 43.1 | 42.8 | 49.1 | 48.7 | 49.1 | 48.7 |
| 19 | 35.5 | 35.2 | 35.5 | 35.3 | 36.9 | 36.7 | 36.8 | 36.7 |
| 20 | 28.3 | 28.2 | 28.3 | 28.2 | 29.0 | 28.8 | 28.9 | 28.8 |
| 21 | 33.1 | 32.8 | 33.1 | 32.8 | 33.4 | 33.1 | 33.39 | 33.1 |
| 22 | 39.5 | 39.3 | 39.4 | 39.3 | 35.3 | 35.1 | 35.3 | 35.1 |
| 23 | 12.5 | 11.6 | 10.6 | 9.9 | 28.6 | 28.0 | 29.2 | 28.2 |
| 24 | 17.0 | 16.4 | 14.8 | 14.6 | 16.4 | 15.44 | 22.6 | 22.2 |
| 25 | 18.6 | 18.2 | 18.3 | 18.1 | 15.7 | 15.41 | 15.6 | 15.2 |
| 26 | 20.3 | 20.1 | 20.3 | 20.2 | 26.2 | 25.9 | 26.3 | 26.0 |
| 27 | 18.9 | 18.6 | 18.8 | 18.6 | 21.5 | 21.3 | 21.4 | 21.2 |
| 28 | 32.3 | 32.1 | 32.2 | 32.1 | 30.0 | 29.8 | 30.0 | 29.8 |
| 29 | 35.1 | 35.0 | 35.0 | 35.0 | 33.4 | 33.3 | 33.37 | 33.3 |
| 30 | 32.0 | 31.8 | 31.9 | 31.8 | 30.0 | 29.9 | 30.0 | 29.9 |

TABLE 2

¹H and ¹³C NMR Data of Ingols EN 26 to EN 29[a]

| No. | EN 26 ¹³C | ¹H | EN 27 ¹³C | ¹H | EN 28 ¹³C | ¹H | EN 29 ¹³C | ¹H |
| --- | --- | --- | --- | --- | --- | --- | --- | --- |
| 1 | 32.2 | 1.67 (d, 14.5)/ 2.79 (dd, 14.5/9.0) | 32.3 | 1.68 (d, 14.5)/ 2.81 (dd, 14.5/9.0) | 32.2 | 1.65 (d, 14.5)/ 2.79 (dd, 14.5/8.4) | 32.3 | 1.64 (d, 14.5)/ 2.79 (dd, 14.5/8.4) |
| 2 | 30.7 | 2.44 (m) | 30.7 | 2.45 (q, 9.0) | 30.6 | 2.44 (m) | 30.7 | 2.42 (q, 8.4) |
| 3 | 77.7 | 5.39 (d, 8.5) | 78.5 | 5.41 (d, 8.5) | 78.0 | 5.32 (d, 9.0) | 78.2 | 5.23 (d, 8.4) |
| 4 | 75.0 | — | 75.0 | — | 75.0 | — | 75.0 | — |
| 5 | 119.1 | 5.75 (s) | 119.3 | 5.80 (s) | 118.7 | 5.65 (s) | 118.9 | 5.80 (s) |
| 6 | 140.3 | — | 140.3 | — | 141.2 | — | 140.9 | — |
| 7 | 78.5 | 4.69 (d, 1.5) | 78.5 | 5.13 (d, 2.0) | 75.8 | 5.31 (s) | 76.3 | 5.50 (d, 1.2) |
| 8 | 72.6 | 4.68 (dd, 1.5/10.5) | 73.3 | 4.88 (dd, 11.0/2.0) | 79.7 | 3.15 (d, 10.2) | 79.9 | 3.26 (d, 12.0) |
| 9 | 208.8 | — | 208.8 | — | 209.2 | — | 209.1 | — |
| 10 | 72.5 | — | 72.6 | — | 72.4 | — | 72.5 | — |
| 11 | 44.2 | 2.99 (m) | 44.2 | 3.04 (m) | 44.2 | 2.98 (m) | 44.2 | 3.03 (m) |
| 12 | 72.3 | 4.89 (dd, 4.0/11.5) | 72.3 | 4.96 (dd, 11.0/4.0) | 72.9 | 4.93 (dd, 10.8/4.2) | 72.9 | 4.97 (dd, 11.4/4.2) |
| 13 | 32.3 | 1.10 | 32.4 | 1.18[b] | 32.2 | 0.96[b] | 32.2 | 1.06 (m) |
| 14 | 26.5 | 1.43 (dd, 11.0/9.5) | 26.6 | 1.55 (dd, 10.5/9.0) | 28.9 | 1.24 (t, 9.6) | 28.7 | 1.39 (t, 9.6) |
| 15 | 20.5 | — | 20.6 | — | 20.5 | — | 20.5 | — |
| 16 | 16.7 | 0.79 (s) | 16.7 | 0.81 (s) | 17.1 | 0.96 (s) | 17.2 | 0.99 (s) |
| 17 | 29.3 | 1.09 (s) | 29.4 | 1.14 (s) | 29.6 | 1.04 (s) | 29.6 | 1.10 (s) |
| 18 | 13.8 | 1.02 (d, 7.0) | 13.8 | 1.05 (d, 7.5) | 13.9 | 1.01 (d, 7.2) | 13.9 | 1.03 (d, 7.8) |
| 19 | 17.4 | 0.97 (d, 7.5) | 17.4 | 0.99 (d, 7.5) | 17.3 | 0.94 (d, 7.2) | 17.3 | 0.92 (d, 7.8) |
| 20 | 17.6 | 2.08 (s) | 17.7 | 2.13 (s) | 17.8 | 2.09 (s) | 17.9 | 2.14 (s) |
| 3-OC=OCH₃ | 172.0/20.4 | 2.03 (s) | 172.0/20.4 | 2.03 (s) | 171.9/20.4 | 2.03 (s) | 171.9/20.3 | 2.00 (s) |
| 7-OC=OCH₃ | 171.6/20.8 | 2.10 (s) | 171.7/20.8 | 2.11 (s) | — | — | — | — |
| 12-OC=OCH₃ | 172.2/20.9 | 2.06 (s) | 172.2/20.9 | 2.06 (s) | 172.5/20.9 | 2.07 (s) | 172.4/20.9 | 2.08 (s) |
| C₆H₅C=O | — | — | 131.0/130.5/ | 7.98 (d, 8.5)/7.49 | — | — | 131.4/130.6/ | 8.04 (d, 7.8)/ |

TABLE 2-continued

¹H and ¹³C NMR Data of Ingols EN 26 to EN 29[a]

| No. | EN 26 ¹³C | EN 26 ¹H | EN 27 ¹³C | EN 27 ¹H | EN 28 ¹³C | EN 28 ¹H | EN 29 ¹³C | EN 29 ¹H |
|---|---|---|---|---|---|---|---|---|
| | | | 129.8/134.6/ 167.3 | (dd, 8.5/7.5)/7.61 (t, 7.5) | | | 129.6/134.4/ 167.1 | 7.48 (t, 7.8)/ 7.60 (t, 7.8) |
| 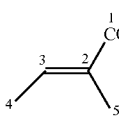 | 168.7/129.5/ 139.5/14.5/ 12.0 | 6.86 (m)/1.81/ 1.81 | — | — | — | — | — | — |
| 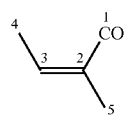 | — | — | — | — | 168.3/129.2/ 139.2/16.1/ 20.7 | 6.12 (q, 7.2)/ 1.96 (d, 7.21)/1.92 (s) | — | — |
| 8-OCH₃ | — | — | — | — | 56.7 | 3.33 (s) | 56.7 | 3.37 s) |

[a] measured in CD₃OD, multiplicity and coupling constant (J in Hz) are assigned in parentheses; br. s, broad singlet; d, doublet: dd, double doublet: s, singlet: t, triplet.
[b] Signal patterns are unclear due to overlapping.

Example 2

Anti-Proliferative Activity of the Compounds of this Invention 2.1 EN 22, EN 24, or EN 25 Inhibits In Vitro Growth of Human Esophageal Squamous 81T/VGH Cells Effects of the compounds of formula (I) of this disclosure, particularly, EN 22, EN 24, and EN 25, on 81T/VGH cells were assessed by cell viability analysis in accordance with procedures described above. Results are summarized in Table 3.

TABLE 3

Growth Inhibition On Esophageal Squamous Cells

| Compound | | Inhibition (%) 1 μM | Inhibition (%) 10 μM |
|---|---|---|---|
| EN 22 | 24 hrs | 51.98 | 58.03 |
| | 48 hrs | 41.42 | 58.61 |
| EN 24 | 24 hrs | 49.15 | 63.99 |
| | 48 hrs | 43.47 | 57.10 |
| EN 25 | 24 hrs | 49.45 | 61.74 |
| | 48 hrs | 39.99 | 62.55 |

It is evident that, after treatment for 24 hrs, the cell number of human esophageal squamous 81T/VGH cells is reduced for about 50% in the presence of 1 μM of any of the tested compounds, and is further reduced for about 60% if the concentration of the test compound(s) is raised to 10 μM.

2.2 EN 22 Reduces Tumor Size in Animals Grafted with Human Esophageal Squamous 81T/VGH Cancer Cells Mice were inoculated with esophageal squamous tumor cells in accordance with the procedures described above. For in vivo therapy, animals were given 2 mg/Kg cisplatin intraperitoneally, in the presence or absence of 20 mg/Kg EN 22, which was given orally, for a period of at least 4 weeks. Tumor size, body weight, white blood cell count, and liver function of each animal were then measured respectively at the indicated time. Results are depicted in FIGS. 1 to 3, respectively.

Figure 2:
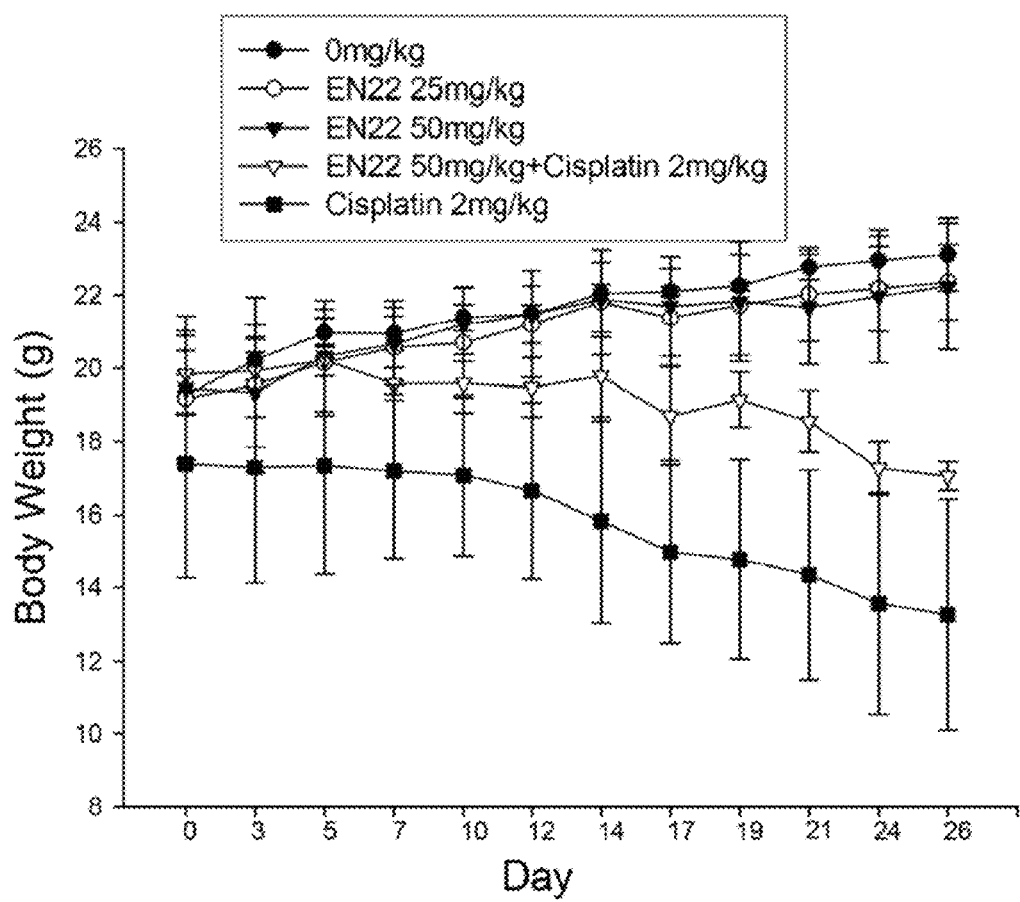
FIG. 2 illustrates the effects of EN 22 on body weight loss in cisplatin-treated animals in accordance with one embodiment of this invention.

FIG. 1 illustrates the effects of EN 22 on the tumor size of cisplatin-treated animals. As depicted in FIG. 1, as the tumor progressed, its size increased with time. The conventional chemotherapeutic agent—cisplatin, at a dose of 2 mg/Kg, was capable of suppressing the growth of tumor during the entire treatment period. Similarly, EN 22, though not as potent as cisplatin, was able to suppress the growth of the tumor in a dose dependent manner, with 50 mg/Kg being more potent than the dose at 20 mg/Kg; and combined treatment with cisplatin (2 mg/Kg) and EN 22 (20 mg/Kg), reduced the tumor size to an extent similar to that of cisplatin (2 mg/Kg) alone.

One major drawback in conventional chemotherapy is that the recipient often suffers from weight lost, which compromises the treatment effect if the recipient failed to maintain a healthy weight. Refers to both FIGS. 1 and 2, thought cisplatin is effective in suppressing tumor growth (FIG. 1), yet animals suffer a nearly 40% lost in body weight (FIG. 2). EN 22, though mild in suppressing tumor growth, was free from the "weight lost" problem that is commonly associated with the use of a chemotherapeutic agent; and when the animals were treated with both EN 22 (50 mg/Kg) and cisplatin (2 mg/Kg), such combined treatment greatly alliviating the "weight lost" problem that often associated with the administration of cisplatin.

Figure 3:
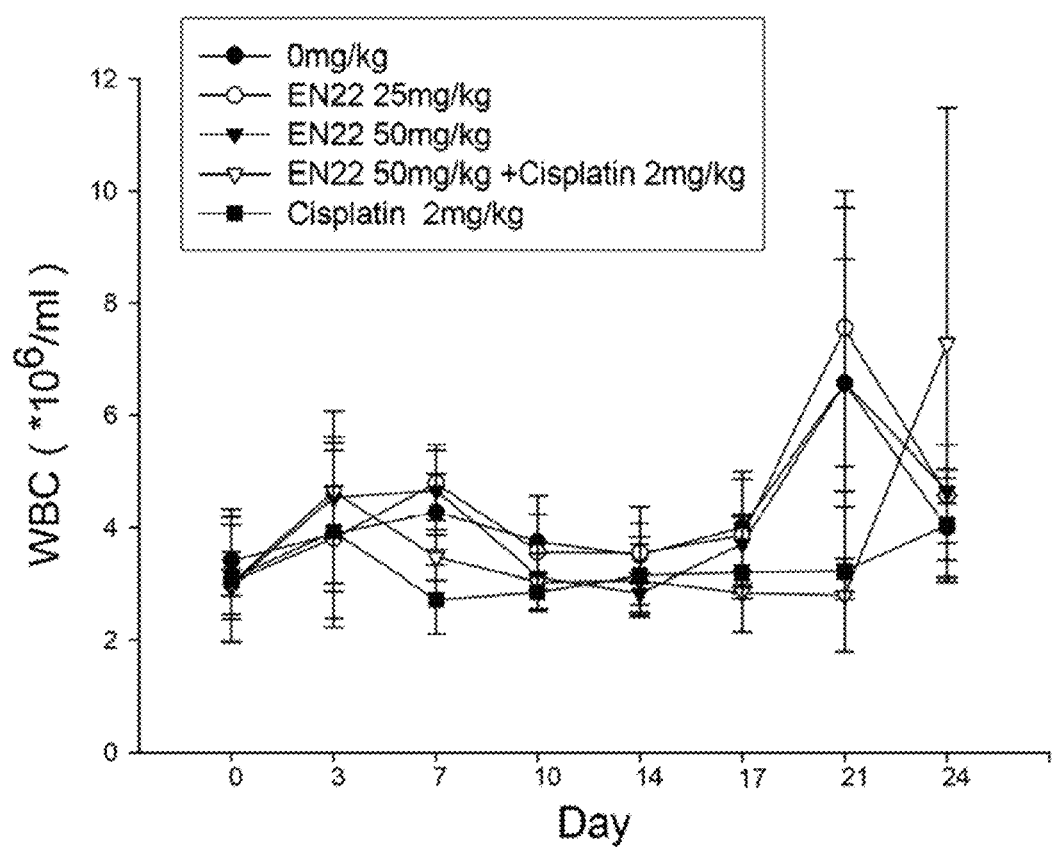
FIG. 3 illustrates the effects of EN 22 on white blood cell counts in cisplatin-treated animals in accordance with one embodiment of this invention.

The effects of EN 22 on white blood cell (WBC) counts in cisplatin-treated animals are depicted in FIG. 3. The tested dosage of EN 22 (25 or 50 mg/Kg), was capable of suppressing tumor growth, yet it did not affect the number of WBC. Similar results were also observed in animals treated with cisplatin (2 mg/Kg). 2.3 EN 22, EN 26, or EN 28 Inhibits In Vitro Growth of Human Chronic Myelogenous Leukemia (CML) K562 Cells and/or Humane Erythroleukemia (HEL) cells Effects of the compounds of formula (I) or (II) of this disclosure, particularly, EN 22, EN 26, and EN 28, on K562 cells were assessed by cell viability analysis in accordance with procedures described above. Results are summarized in Table 4 and FIG. 4.

TABLE 4

Growth Inhibition On Chronic Myelogenous Leukemia Cells

| Compound | | Inhibition (%) 10 μM |
|---|---|---|
| EN 22 | 24 hrs | 17.94 |
|  | 48 hrs | 39.32 |
|  | 72 hrs | 45.38 |
| EN 26 | 24 hrs | 12.74 |
|  | 48 hrs | 30.38 |
|  | 72 hrs | 42.35 |
| EN 28 | 24 hrs | 22.11 |
|  | 48 hrs | 44.85 |
|  | 72 hrs | 52.52 |

Figure 4:
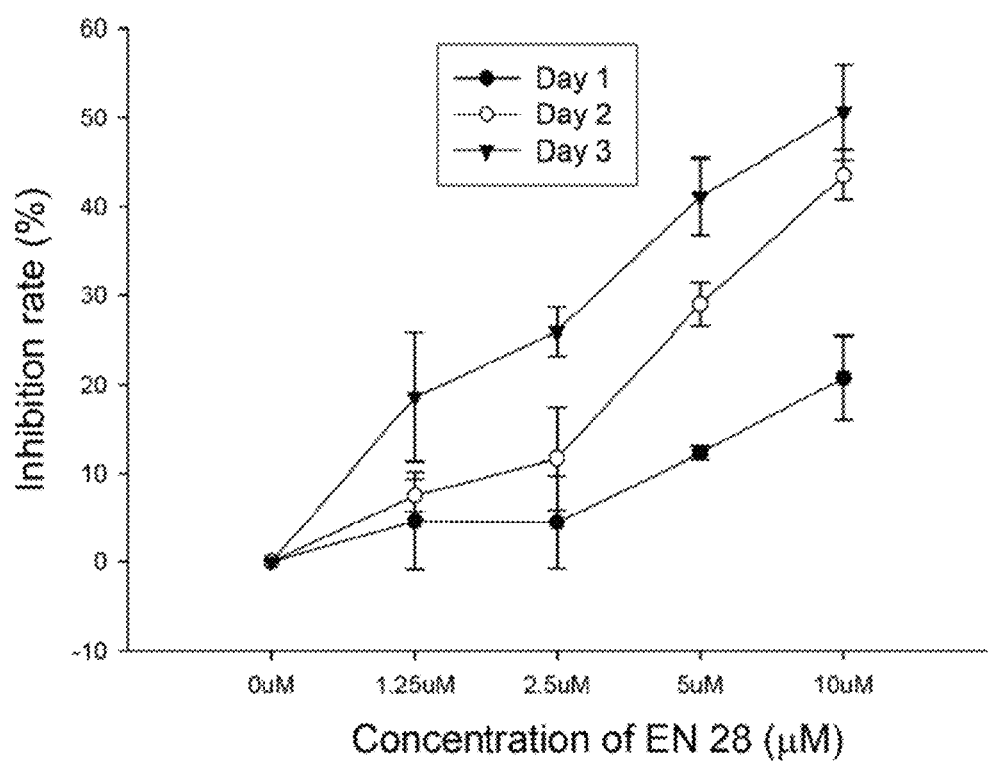
FIG. 4 illustrates the effects of EN 28 on in vitro growth inhibition in K562 cells in accordance with one embodiment of this invention.
Figure 5:
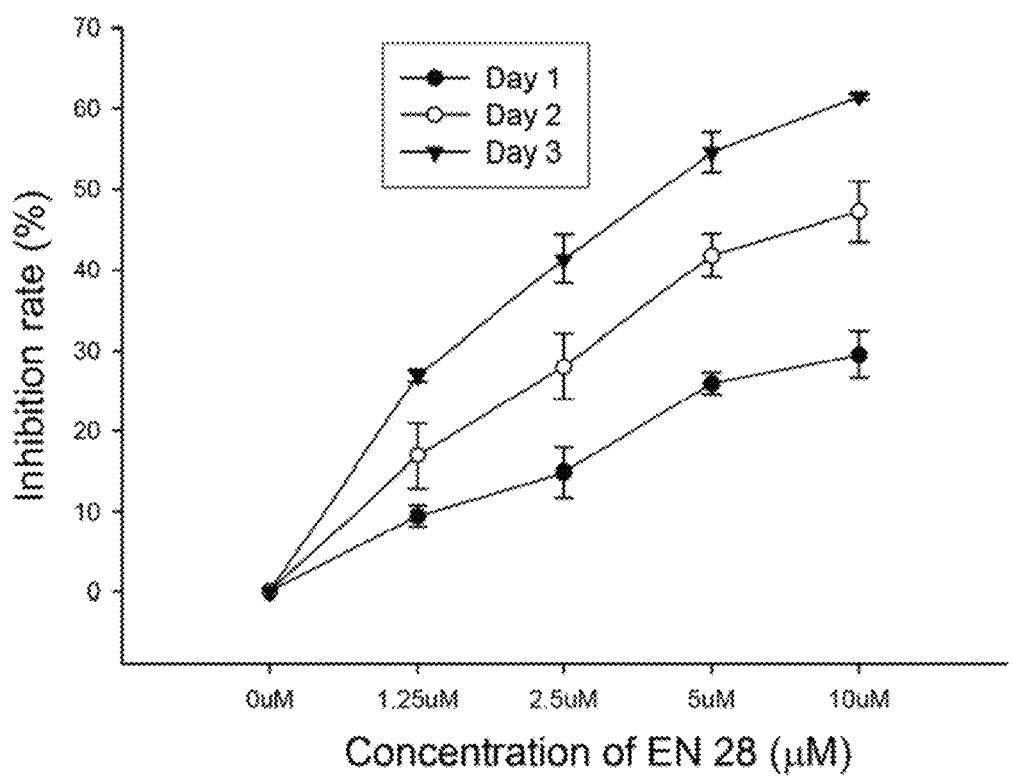
FIG. 5 illustrates the effects of EN 28 on in vitro growth inhibition in HEL cells in accordance with one embodiment of this invention.

As evident from Table 4, the compound of formula (II) (e.g., EN 28) seems slightly more potent than the compound of formula (I) (e.g., EN 22) in terms of growth inhibition on human Chronic myelogenous leukemia K562 cells. After treatment for 24 hrs, K562 cell number decreased for about 20% in the presence of 10 μM EN 28, whereas EN 22 resulted in about 17% growth inhibition. As the treatment time of EN 28 increased to 72 hrs, about 50% growth inhibition was observed. A dose dependent curve on in vitro growth inhibition of K562 cells is depicted in FIG. 4. Similar results were also found for HEL cells (FIG. 5).

Example 3

Thromobocytopoletic Effects of Compounds of Formula (II)

3.1 EN 28 Enhances the Maturation of Megakaryocytes

Figure 6:
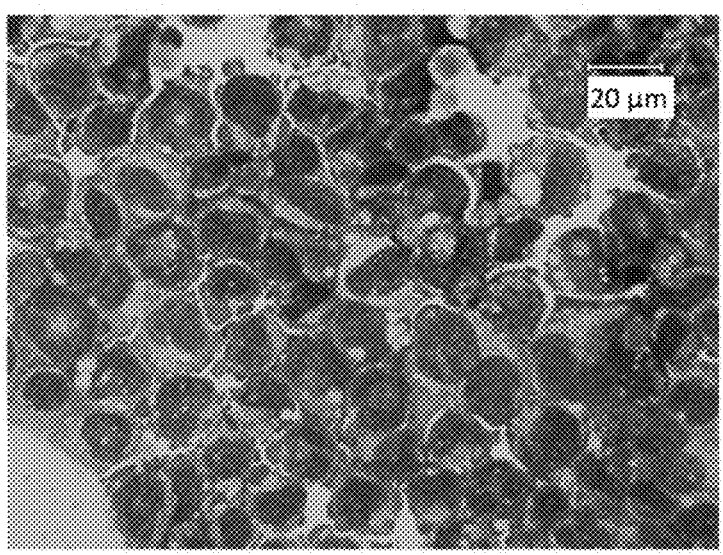
FIG. 6 are photographs of CML K562R cells identified by Liu's staining in accordance with one embodiment of this invention, in which (A) is the control cells, (B) is 10 μM EN 28-treated cells for 9 days.
Figure 6:
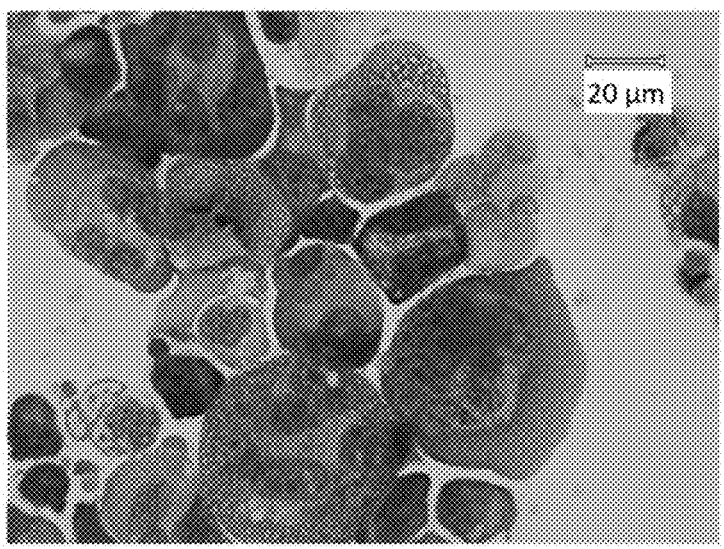
Figure 7:
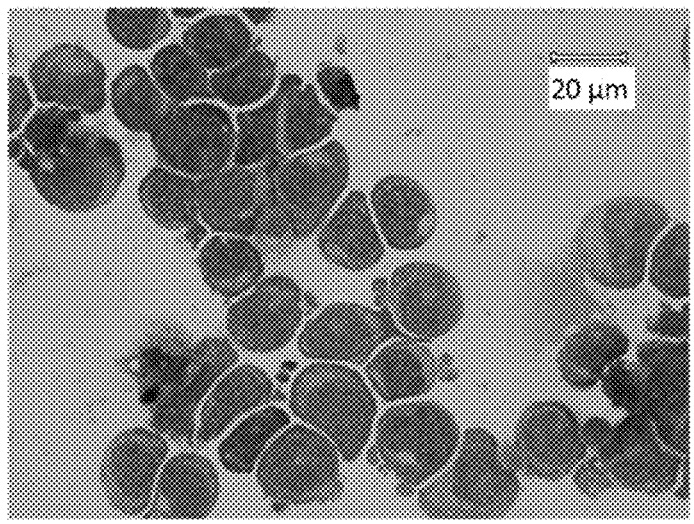
FIG. 7 are photographs of HEL cells identified by Liu's staining in accordance with one embodiment of this invention, in which (A) is the control cells, (B) is 10 μM EN 28-treated cells for 5 days.
Figure 7:
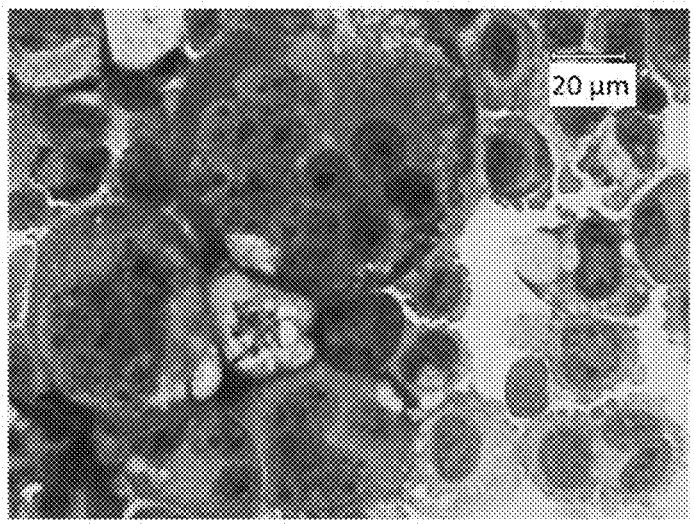
Figure 8:
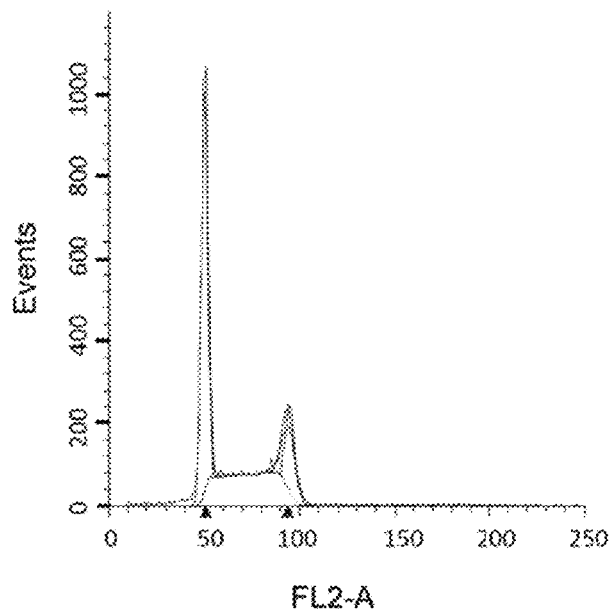
FIG. 8 illustrates the cell cycle analysis in the control and EN 28-treated HEL cells respectively in accordance with one embodiment of this invention.
Figure 8:
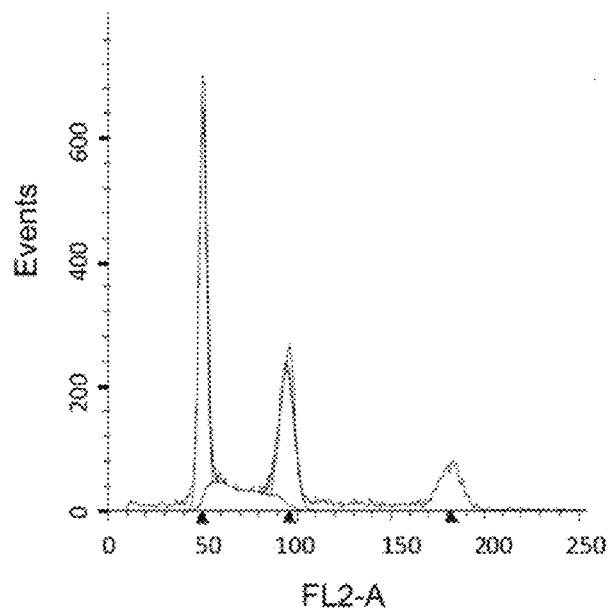

Megarkaryocytopoiesis is a process by which bone marrow progenitor cells develop into mature megakaryocytes, which in turn produce platelets required for normal hemostasis. In this study, the inventor unexpectedly discovered that K562 cells, when continuously treated with EN 28 at a dose of 10 μM for 9 days, their morphology changed, as cells started to fuse and form megakaryocytes (FIG. 6). Similar results were also observed in HEL cells (FIG. 7). Cell cycle analysis further confirmed that EN 28 is capable of inducing the generation of new population of cells (FIG. 8).

Figure 9:
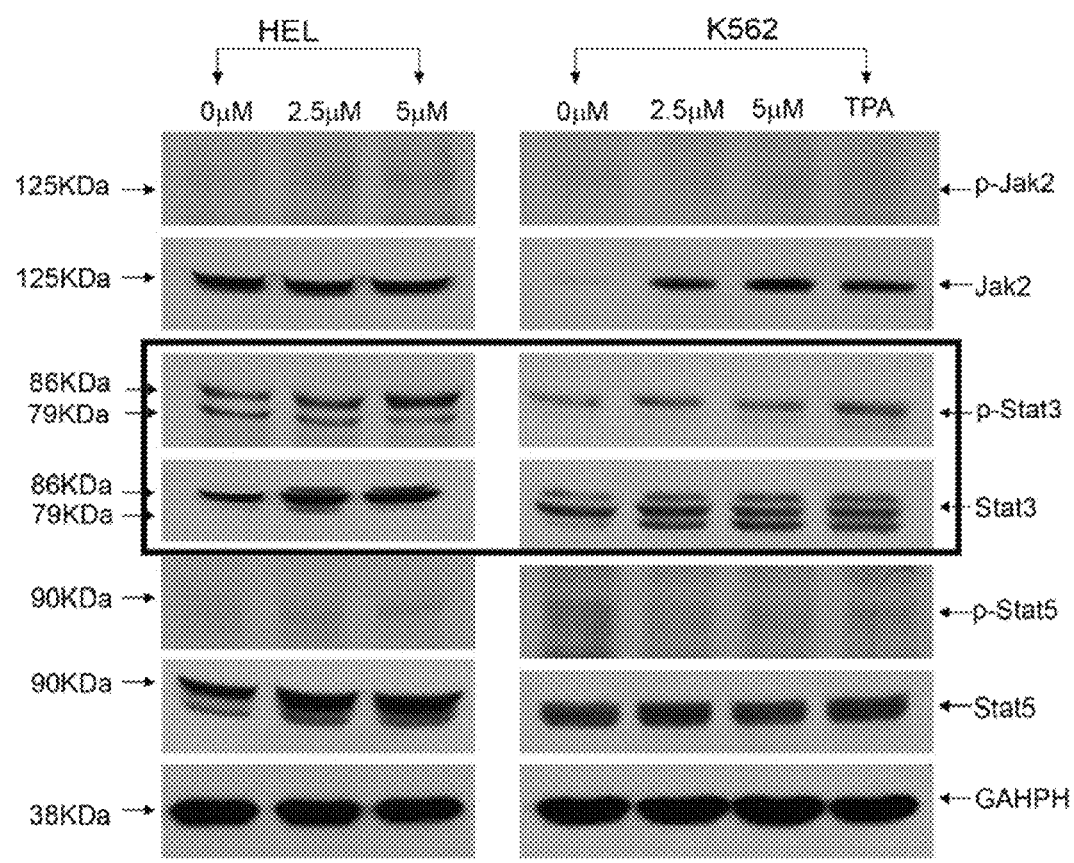
FIG. 9 illustrates the expressed level of phosphorylated proteins in EN 28-treated HEL cells in accordance with one embodiment of this invention.
Figure 10:
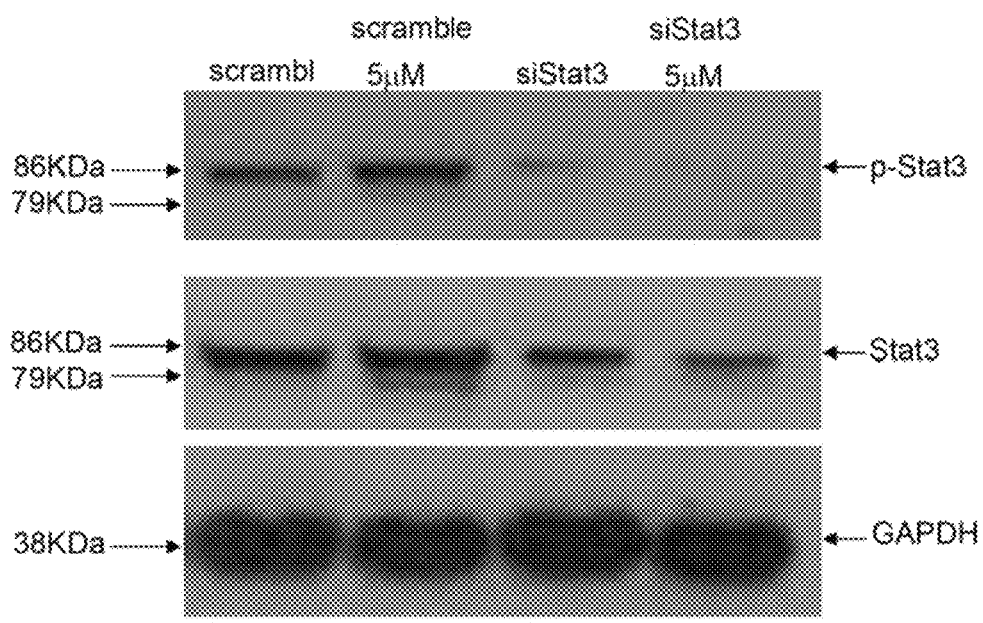
FIG. 10 illustrates the knockdown of Stat3 gene by small interference RNA in accordance with one embodiment of this invention; in which scrambled RNA is used as a control for specific knockdown.

The induction of K562 cells or HEL cells to form megakaryocytes was further investigated by measuring the expressed level of its regulatory proteins such as, stat3 and phosphorylated stat3. It was found that both the levels of stat3 and phosphorylated stat-3 increased in EN 28-treated K562 cells and HEL cells, respectively (FIG. 9); as compared with that of the control. Further, the induction of megakaryocytic differentiation in HEL cells was partially reversed by the knockdown of Stat3 using a small interference RNA, which further substantiates the involvement of Stat3 in megakaryocytic differentiation process (FIG. 10).

Figure 11:
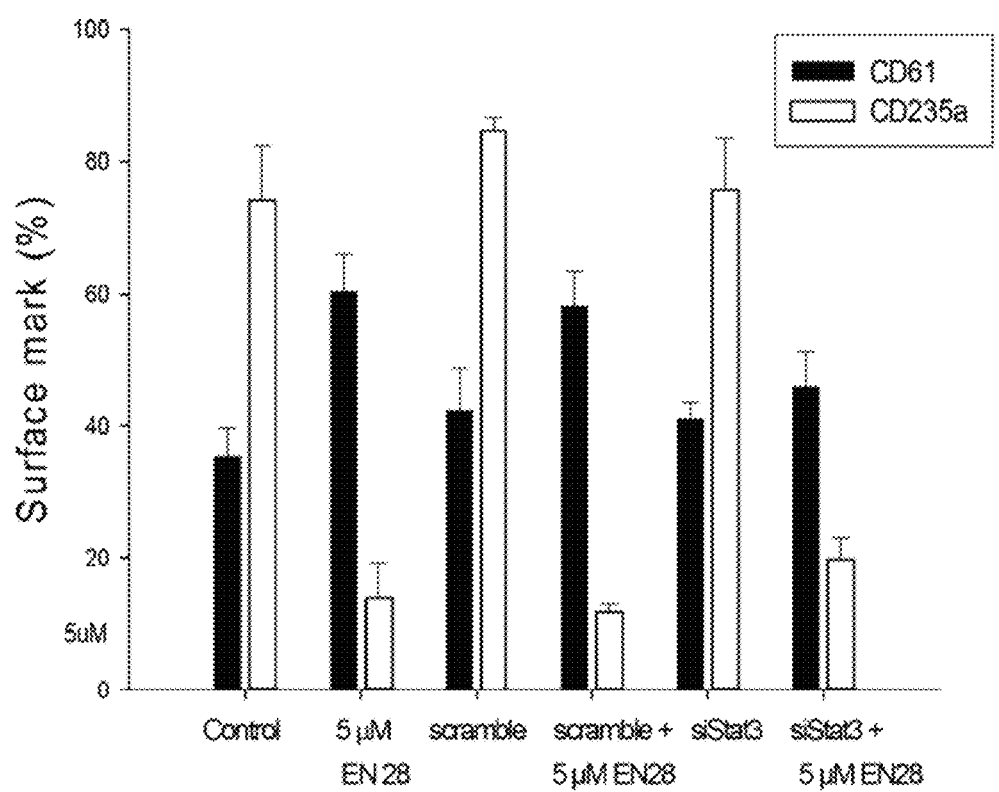
FIG. 11 illustrates the flow cytometric analysis of CD61 and CD235a expression in the control and EN 28-treated HEL cells, respectively in accordance with one embodiment of this invention.

The induction of megakaryocytic differentiation may also be confirmed by the measurement of the differentiation markers CD61 and CD235a expressed on the erythrocyte membrane during the differentiation stage. As depicted in FIG. 11, treatment with 5 μM EN 28 resulted in the up-regulation of CD61, as well as the down-regulation of CD235a in HEL cells; and such effects were not antagonized by the knockdow of siStat3 gene.

Figure 12:
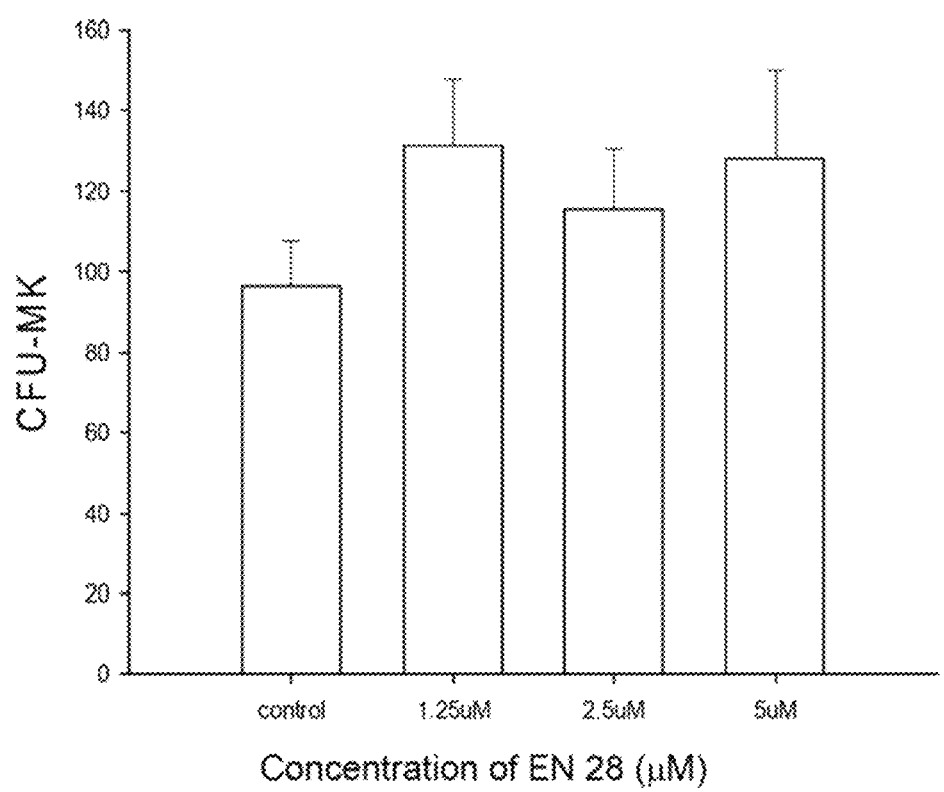
FIG. 12 illustrates the effect of EN 28 on the induction and proliferation of megakaryocytes from normal bone marrow cells in accordance with one embodiment of this invention.

Even for normal bone marrow cells, EN 28, at a low dose of 1.25 μM, was capable of inducing the proliferation and subsequently, the differentiation of the proliferated normal bone marrow cells into megakaryocytes (FIG. 12).

The foregoing description of various embodiments of the disclosure has been presented for purpose of illustration and description. It is not intended to be exhaustive or to limit the disclosure to the precise embodiments disclosed. Numerous modifications or variations are possible in light of the above teachings. The embodiments discussed were chosen and described to provide the best illustration of the principles of the disclosure and its practical application to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method of suppressing the growth of leukemia cells, or inducing the leukemia cells or bone marrow cells to differentiate into megakaryocytes comprising contacting the leukemia cells or bone marrow cells with a sufficient amount of a compound of formula (II), or a pharmaceutically acceptable salt thereof

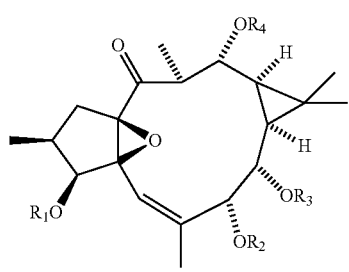

wherein
each $R_1$ and $R_4$ is independently —$COCH_3$;
$R_2$ is —$COCH_3$,

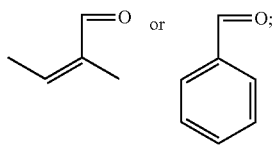

and
$R_3$ is —$CH_3$,

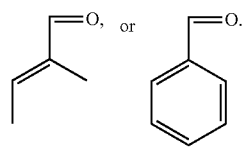

2. The method of claim 1, wherein in the compound of formula (II), each $R_1$ and $R_4$ is independently —$COCH_3$; $R_2$ is

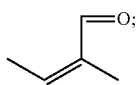

and $R_3$ is —$CH_3$.

3. The method of claim 2, wherein the sufficient amount of the compound is from about 1.25 μM to 10 μM.

4. The method of claim 2, wherein the leukemia cells are chronic myelogenous leukemia cells or erythroleukemia cells; and the bone marrow cells are normal bone marrow cells.

5. A method of treating leukemia or thrombocytopenia comprising administering to a subject an effective amount of a compound of formula (II), or a pharmaceutically acceptable salt thereof,

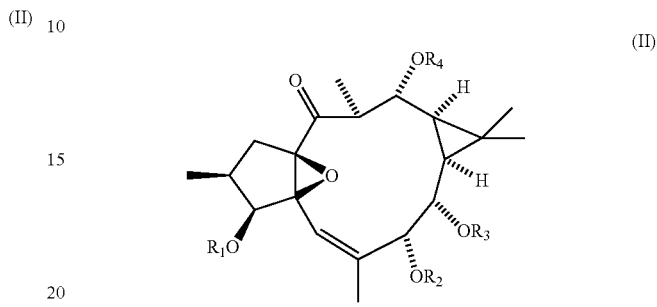

wherein
each $R_1$ and $R_4$ is independently —$COCH_3$;
$R_2$ is —$COCH_3$,

and
$R_3$ is —$CH_3$,

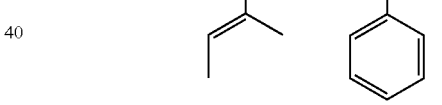

6. The method of claim 5, wherein in the compound of formula (II), each $R_1$ and $R_4$ is independently —$COCH_3$; $R_2$ is

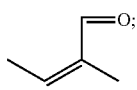

and $R_3$ is —$CH_3$.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Mus musculus

<400> SEQUENCE: 1
tggcccaatg gaatcagcta cagca                                           25

<210> SEQ ID NO 2
<211> LENGTH: 25
<212> TYPE: RNA
<213> ORGANISM: artificial sequence
<220> FEATURE:
<223> OTHER INFORMATION: siRNA sense strand for murine stat3 target
      sequence

<400> SEQUENCE: 2
uggcccaaug gaaucagcua cagca                                           25
```